United States Patent [19]

Bennett

[11] 4,013,767

[45] Mar. 22, 1977

[54] 3-PYRIDYL AND PYRIDYL-N-OXIDE-FURO[3,4-E]-AS-TRIAZINES

[75] Inventor: Gregory B. Bennett, Mendham, N.J.

[73] Assignee: Sandoz, Inc., E. Hanover, N.J.

[22] Filed: Aug. 15, 1975

[21] Appl. No.: 605,069

[52] U.S. Cl. .......................... 424/249; 260/248 AS
[51] Int. Cl.$^2$ ................ C07D 253/08; A61K 31/53
[58] Field of Search .............. 260/248 AS; 424/249

[56] References Cited

UNITED STATES PATENTS

| | | | |
|---|---|---|---|
| 3,697,518 | 10/1972 | Schmidt et al. | 260/248 |
| 3,772,276 | 11/1973 | Sauter | 260/248 |

Primary Examiner—John M. Ford
Attorney, Agent, or Firm—Gerald D. Sharkin; Robert S. Honor; Timothy G. Rothwell

[57] ABSTRACT

Substituted or unsubstituted-3-pyridyl and pyridyl-N-oxide-furo[3,4-e]-as-triazines, e.g., 5,7-dihydro-3-(2-pyridyl)-5,5,7,7-tetramethyl-furo[3,4-e]-as-triazine are prepared by reacting 2,2,5,5-tetramethyl-3,4(2H,5H)furandiones with substituted or unsubstituted pyridylcarboxamidic acid hydrazides and are useful as sleep inducers and minor tranquilizers.

9 Claims, No Drawings

3-PYRIDYL AND PYRIDYL-N-OXIDE-FURO[3,4-E]-AS-TRIAZINES

This invention relates to 3-pyridyl and pyridyl-N-oxide-furo[3,4-e]-as-triazines which exhibit sleep-inducer and minor tranquilizer activity. In particular, it relates to substituted or unsubstituted 3-pyridyl and pyridyl-N-oxide-furo[3,4-e]-as-triazines, their pharmaceutically acceptable salts and to their preparation.

The compounds of this invention may be represented by the following structural formula:

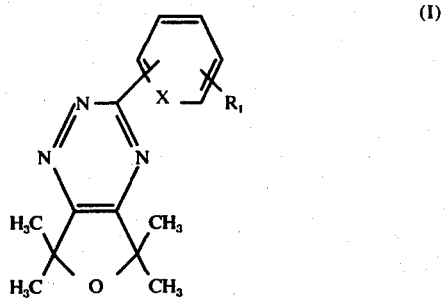

(I)

wherein
R₁ represents hydrogen, halo having an atomic weight of about 19 to 36, lower alkyl, i.e. alkyl having 1 to 4 carbon atoms, e.g. methyl, ethyl, isopropyl and the like, straight chain lower alkoxy, i.e. straight chain alkoxy having 1 to 4 carbon atoms, e.g. methoxy, ethoxy and the like, or trifluoromethyl, and x represents N or N → O
provided that when R₁ represents t-butyl, or trifluoromethyl, R₁ and the triazine ring are on other than adjacent carbon atoms.

The compounds of formula (I) in which X represents N may be prepared according to the following reaction scheme:

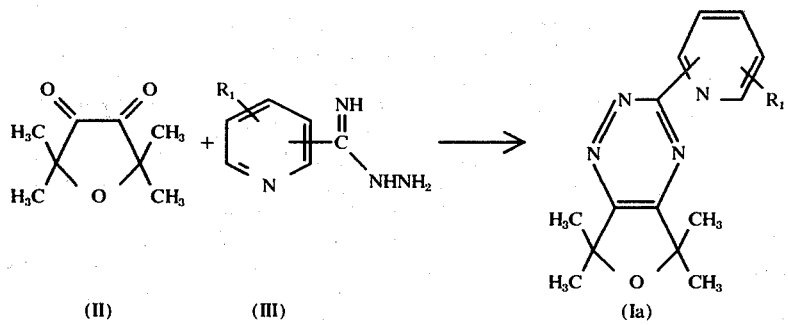

where R₁ and X are as defined above.

The compounds of formula (Ia) are prepared by treating a compound of the formula (II) with a compound of the formula (III) in the presence of an inert atmosphere, e.g., nitrogen, helium, or argon, preferably nitrogen, and in the presence of an inert, organic solvent. Although the particular solvent used is not critical, the preferred solvents include an aromatic hydrocarbon such as benzene, toluene, and the like, or a lower alkanol, such as methanol, ethanol and the like, preferably ethanol. The temperature of the reaction is not critical, but it is preferred that the reaction be run from about 20° to 150° C., more preferably from about 35° to 80° C. The reaction is run from about 1 to 36 hours, preferably from about 8 to 18 hours. The product is recovered using conventional techniques, e.g., recrystallization.

The compounds of formula (I) in which X represents N → O may be prepared according to the following reaction scheme:

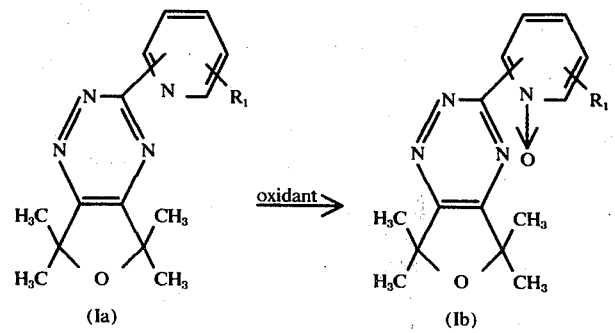

where R₁ is as defined above.

The compounds of formula (Ib) are prepared by reacting a compound of the formula (Ia) with an oxidizing agent in the presence of an inert organic solvent. The particular oxidizing agent employed is not critical, but it is preferred that the aliphatic and aromatic percarboxylic acids be utilized including peracetic acid, perbenzoic acid, m-chlorobenzoic acid and the like or hydrogen peroxide, preferably m-chlorobenzoic acid. When the hydrogen peroxide is employed as the oxidizing agent, it is preferred that an acidic solvent, such as acetic acid, trifluoroacetic acid or dilute sulfuric acid be used, especially acetic acid. However, when the percarboxylic acids are employed, the particular solvent utilized is not critical, and may include an aromatic hydrocarbon such as toluene, benzene and the like, or a halogenated hydrocarbon such as methylene chloride, chloroform and the like, preferably chloroform. The temperature of the reaction is not critical, but it is preferred that the reaction be run from about −5° to 100° C., preferably from about 30° to 65° C. The reaction is run from about 4 to 72 hours, preferably from about 18 to 48 hours. The product is removed using conventional techniques, e.g. recrystallization.

Many of the compounds of formulae (II) and (III) are known and may be prepared by methods described in the literature, for example, Journal of Organic Chemistry, Vol. 31, 1965, p. 931, and Journal of General Chemistry, Vol. 24, 1954, p. 188. The compounds of formulae (II) and (III) not specifically described may be prepared from known starting materials by analogous methods.

The compounds of formula (I) are useful because they possess pharmacological activity. In particular, the compounds are useful as central nervous system depressants, especially as sleep inducers and minor tranquilizers, as indicated by (1) their ability to produce docility in behavior tests in mice given 25 to 200 mg/kg of animal body weight, i.p. of the test compound according to the 30-word adjective check sheet system basically as described by Irwin S. Gordon (Research Conference, Medicinal Chemistry, [1959]) and Chen (Symposium on Sedative and Hypnotic Drugs, Williams and Wilkins, 1954); (2) by their ability to antagonize chronic convulsions and death in mice given 33 to 125 mg/kg i.p. of N-sulfamoylazepine; (3) by the hexobarbital reinduction method of Winter, J. Pharmacol and Exp. Therap., 94, 7–11, 1948) in which the reinduction of anesthesia after recovery from hexobarbital induces anesthesia is used to determine sedative-hypnotic activity in mice given 70 mg/kg of animal body weight, i.p. of hexobarbital followed immediately after the mice regain their righting reflexes by 25 to 200 mg/kg of animal body weight, i.p. of the test compound; and (4) by scoring for loss of righting reflex according to the method of Reed-Muench (American Journal of Hygiene, 27:493–497, 1938) in which mice are administered 12.5 mg/kg i.p. thioridazine, immediately after which test compound is administered at dosages of 5 to 150 mg/kg in a volume of 0.1 ml/10 g. body weight. Thirty minutes after dosing, the mice are scored for loss of righting reflex.

For such usage, the compounds may be administered orally or parenterally as such or admixed with conventional pharmaceutical carriers.

The dosage of active ingredient employed for minor tranquilizer use may vary depending on the severity of the condition being treated. However, in general, satisfactory results are obtained when a compound of formula (I) is administered at a daily dosage of from about 2 milligrams to about 200 milligrams per kilogram of animal body weight p.o., preferably given in divided doses two to four times a day, or in sustained release form. For most larger mammals (e.g., primates), the total daily dosage is from about 150 milligrams to about 1500 milligrams. Dosage forms suitable for internal use comprise from about 35 to about 750 milligrams of active compound in intimate admixture with a solid or liquid pharmaceutically acceptable carrier or diluent.

The dosage of active ingredient employed for sleep inducer use may vary depending on the severity of the condition being treated. However, in general, satisfactory results are obtained when a compound of the formula (I) is administered at a daily dosage of from about 2 milligrams to about 100 milligrams per kilogram of animal body weight p.o., typically given in a single dose at bedtime. For most larger mammals, the total daily dosage is from about 150 milligrams to about 1000 milligrams, preferably at bedtime in a single dose, and dosage forms suitable for internal administration comprise from about 35 to about 500 milligrams of the compound in admixture with a solid or liquid pharmaceutical carrier or diluent. The preferred pharmaceutical compositions from the standpoint of preparation and ease of administration are solid compositions, particularly hard-filled capsules and tablets.

The compounds of formula (I) may be similarly administered in the form of their non-toxic pharmaceutically acceptable salts. Such salts possess the same order of activity as the free base and are readily prepared by reacting the base with an appropriate acid by conventional technique and, accordingly, are included within the scope of this invention. Representative of such salts are the mineral acid salts, e.g., hydrochloride, hydrobromide, sulfate and the like, and the organic acid salts such as succinate, benzoate, maleate and the like.

Tablets and capsules containing the ingredients indicated below may be prepared by conventional techniques and are useful as sleep inducers at a dose of one or two tablets just before bedtime. Tablets and capsules containing the ingredients indicated below may also be useful as minor tranquilizers in divided doses two to four times per day.

| Ingredients | Weight (mg.) | |
|---|---|---|
| | Tablet | Capsule |
| 5,7-dihydro-3-(2-pyridyl-N-oxide)-5,5,7,7,-tetramethylfuro[3,4-e]-as-triazine | 200 | 200 |
| tragacanth | 10 | — |
| lactose | 247.5 | 300 |
| corn starch | 25 | — |
| talcum | 15 | — |
| magnesium stearate | 2.5 | — |
| Total | 500 mg. | 500 mg. |

EXAMPLE 1

5,7-Dihydro-3-(2-pyridyl)-5,5,7,7-tetramethyl-furo[3,4-e]-as-triazine

A mixture of 1.56 g. (0.01 mole) of 2,2,5,5-tetramethyl-3,4(2H,5H)-furandione and 1.36 g. (0.01 mole) 2-pyridyl carboxamidic acid hydrazide in 100 ml. absolute ethanol is refluxed under nitrogen for 18 hours at a bath temperature of 100° C. The excess water is removed from the condensate by using a Dean Stark trap filled with 3A molecular sieves. The resulting mixture is evaporated to dryness in vacuo at 40° C., and the resulting residue is recrystallized from hexane to give 5,7-dihydro-3-(2-pyridyl)-5,5,7,7-tetramethyl-furo[3,4-e]-as-triazine; m.p. 77° to 78° C.

Following the above procedure and using in place of pyridyl-carboxamidic acid hydrazide an equivalent amount of a. 2-(5-chloropyridyl) carboxamidic acid hydrazide,
b. 2-(5-methylpyridyl) carboxamidic acid hydrazide,
c. 2-(4-methoxypyridyl) carboxamidic acid hydrazide, or
d. 2-(4-trifluoromethylpyridyl) carboxamidic acid hydrazide, there is obtained a. 5,7-dihydro-3-(5-chloro-2-pyridyl)-5,5,7,7-tetramethyl-furo[3,4-e]-as-triazine,
b. 5,7-dihydro-3-(5-methyl-2-pyridyl)-5,5,7,7-tetramethyl-furo[3,4-e]-as-triazine,
c. 5,7-dihydro-3-(4-methoxy-2-pyridyl)-5,5,7,7-tetramethyl-furo[3,4-e]-as-triazine, or
d. 5,7-dihydro-3-(4-trifluoromethyl-2-pyridyl)-5,5,7,7-tetramethyl-furo[3,4-e]-as-triazine, respectively.

The 5,7-dihydro-3-(2-pyridyl)-5,5,7,7-tetramethyl-furo[3,4-e]-as-triazine of this example is an effective sleep inducer when orally administered to an animal in need of said treatment at a dosage of 200 mg. just before bedtime. The aforementioned compound is also an effective minor tranquilizer when orally administered to an animal in need of said treatment at a dosage of 150 mg. two to four times per day.

EXAMPLE 2

5,7-Dihydro-3-(2-pyridyl-N-oxide)-5,5,7,7-tetramethyl-furo [3,4-e]-as-triazine

To a solution of 2.56 g (0.01 mole) 5,7-dihydro-3-(2-pyridyl)-5,5,7,7-tetramethyl-furo[3,4-e]-as-triazine in 100 ml. chloroform is added dropwise a solution of 2.04 g. (0.01 mole) of 85% m-chloroperbenzoic acid in 40 ml. chloroform. The resulting solution is stirred at room temperature for 36 hours, washed with 10% aqueous sodium bicarbonate and brine solution, dried over magnesium sulfate, filtered, and the filtrate evaporated to dryness in vacuo. The resulting residue is recrystallized from ether/hexane to give 5,7-dihydro-3-(2-pyridyl-N-oxide)-5,5,7,7-tetramethyl-furo[3,4-e]-as-triazine; m.p. 192°–194° C.

Following the above procedure and using in place of 5,7-dihydro-3-(2-pyridyl)-5,5,7,7-tetramethyl-furo-[3,4-e]-as-triazine an equivalent amount of
a. 5,7-dihydro-3-(5-chloro-2-pyridyl)-5,5,7,7-tetramethyl-furo[3,4-e]-as-triazine,
b. 5,7-dihydro-3-(5-methyl-2-pyridyl)-5,5,7,7-tetramethyl-furo[3,4-e]-as-triazine,
c. 5,7-dihydro-3-(4-methoxy-2-pyridyl)-5,5,7,7-tetramethyl-furo[3,4-e]-as-triazine, or
d. 5,7-dihydro-3-(4-trifluoromethyl-2-pyridyl)-5,5,7,7-tetramethyl-furo[3,4-e]-as-triazine,
there is obtained
a. 5,7-dihydro-3-(5-chloro-2-pyridyl-N-oxide)-5,5,7,7-tetramethyl-furo[3,4-e]-as-triazine,
b. 5,7-dihydro-3-(5-methyl-2-pyridyl-N-oxide)-5,5,7,7-tetramethyl-furo[3,4-e]-as-triazine,
c. 5,7-dihydro-3-(4-methoxy-2-pyridyl-N-oxide)-5,5,7,7-tetramethyl-furo[3,4-e]-as-triazine, or
d. 5,7-dihydro-3-(4-trifluoromethyl-2-pyridyl-N-oxide)-5,5,7,7-tetramethyl-furo[3,4-e]-as-triazine, respectively.

The 5,7-dihydro-3-(2-pyridyl-N-oxide)-5,5,7,7-tetramethyl-furo[3,4-e]-as-triazine of this example is an effective sleep inducer when orally administered to an animal in need of said treatment at a dosage of 200 mg. just before bedtime. The aforementioned compound is also an effective minor tranquilizer when orally administered to an animal in need of said treatment at a dosage of 150 mg. two to four times per day.

What is claimed is:
1. A compound of the formula

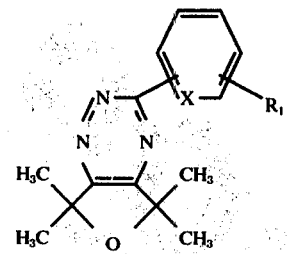

wherein
$R_1$ represents hydrogen, halo having an atomic weight of about 19 to 36, lower alkyl, straight chain lower alkoxy, or trifluoromethyl and
X represents N or N → O,
provided that when $R_1$ represents t-butyl or trifluoromethyl, $R_1$ and the triazine ring are on other than adjacent carbon atoms,
or a pharmaceutically acceptable salt thereof.

2. A compound of the formula

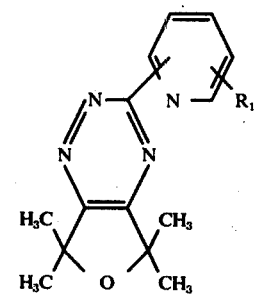

where
$R_1$ and the proviso are as defined in claim 1, or a pharmaceutically acceptable salt thereof.

3. A compound of the formula

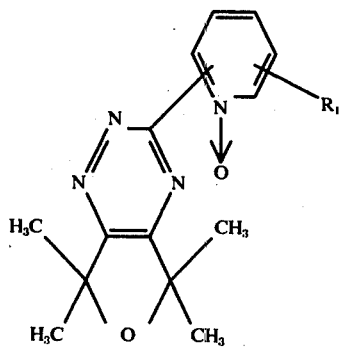

where
$R_1$ and the proviso are as defined in claim 1, or a pharmaceutically acceptable salt thereof.

4. A compound of the formula

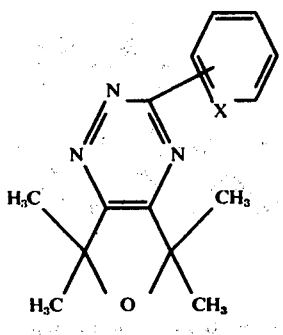

where

X and the proviso are as defined in claim 1, or a pharmaceutically acceptable salt thereof.

5. The compound of claim 2 which is 5,7-dihydro-3-(2-pyridyl)-5,5,7,7-tetramethyl-furo[3,4-e]-as-triazine.

6. The compound of claim 3 which is 5,7-dihydro-3-(2-pyridyl-N-oxide)-5,5,7,7-tetramethyl-furo[3,4-e]-as-triazine.

7. A method of inducing sleep which comprises administering to an animal in need of said treatment a compound according to claim 1 at a daily dosage of from about 150 to about 1000 milligrams.

8. A method of treating tension which comprises administering to an animal in need of said treatment a compound according to claim 1 at a daily dosage of from about 150 to about 1500 milligrams.

9. A pharmaceutical composition comprising an effective amount of a compound of claim 1 and a pharmaceutically acceptable diluent or carrier therefor.

* * * * *